United States Patent
Haimerl

(10) Patent No.: US 9,947,110 B2
(45) Date of Patent: Apr. 17, 2018

(54) METHOD FOR ASSISTING THE POSITIONING OF A MEDICAL STRUCTURE ON THE BASIS OF TWO-DIMENSIONAL IMAGE DATA

(71) Applicant: Brainlab AG, Munich (DE)

(72) Inventor: Martin Haimerl, Gilching (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/118,341

(22) PCT Filed: Feb. 13, 2014

(86) PCT No.: PCT/EP2014/052829
§ 371 (c)(1),
(2) Date: Aug. 11, 2016

(87) PCT Pub. No.: WO2015/120892
PCT Pub. Date: Aug. 20, 2015

(65) Prior Publication Data
US 2017/0193674 A1    Jul. 6, 2017

(51) Int. Cl.
*G06K 9/00* (2006.01)
*G06T 7/70* (2017.01)
(Continued)

(52) U.S. Cl.
CPC ............... *G06T 7/70* (2017.01); *A61B 34/10* (2016.02); *A61B 34/20* (2016.02); *A61B 90/37* (2016.02);
(Continued)

(58) Field of Classification Search
CPC ............ A61B 34/20; A61B 2034/301; A61B 2034/2048; A61B 2034/2051; A61B 34/30
(Continued)

(56) References Cited

U.S. PATENT DOCUMENTS 7,594,933 B2    9/2009    Kammerzell et al.
7,885,705 B2    2/2011    Murphy
(Continued)

FOREIGN PATENT DOCUMENTS

EP    1911421 A1    4/2008
WO    2005000140 A2    1/2005
(Continued)

OTHER PUBLICATIONS

Murphy et al., Evaluation of a New Leg Length Measurement Algorithm in Hip Arthroplasty, Clinical Orthopaedics and Related Research., pp. 1-5; Lippincott Williams & Wilkins.
(Continued)

*Primary Examiner* — Charlotte M Baker
(74) *Attorney, Agent, or Firm* — Tucker Ellis LLP

(57) ABSTRACT

A medical data processing method for assisting the positioning of a first medical structure (1) relative to a second medical structure (2), the method being constituted to be executed by a computer and comprising the following steps: —acquiring two-dimensional projection image data comprising two-dimensional projection image information describing a two-dimensional projection image of at least the first medical structure (1); —acquiring registration data comprising registration information describing the registration of the two-dimensional projection image with respect to the first medical structure (1); —acquiring, on the basis of said two-dimensional projection image data, two-dimensional position data comprising position information describing the position of at least one base point (3) and at least one reference point (4) in the two-dimensional projection image; —acquiring, on the basis of the two-dimensional position data, positional relationship data comprising positional relationship information describing the positional relationship between the at least one base point (3) and the
(Continued)

at least one reference point (4) in the two-dimensional projection image; —acquiring three-dimensional position data comprising position information describing the position of the at least one base point (3) and the at least one reference point (4) in three-dimensional anatomical space, in particular relative to the first medical structure (1); —determining, on the basis of the positional relationship data, the registration data and the three-dimensional position data, three-dimensional reference point correspondence data comprising correspondence information describing whether or not the position of the at least one reference point (4) corresponds to the position of the at least one reference point (4) in the two-dimensional projection image.

17 Claims, 1 Drawing Sheet

(51) Int. Cl.
    *A61B 34/10*     (2016.01)
    *A61B 34/20*     (2016.01)
    *A61B 90/00*     (2016.01)
    *G06T 7/00*     (2017.01)

(52) U.S. Cl.
    CPC ...... *G06T 7/0012* (2013.01); *A61B 2034/108* (2016.02); *A61B 2034/2068* (2016.02); *A61B 2090/376* (2016.02); *G06T 2207/10116* (2013.01); *G06T 2207/30008* (2013.01)

(58) Field of Classification Search
    USPC .................................. 382/132, 325; 600/407
    See application file for complete search history.

(56) References Cited

U.S. PATENT DOCUMENTS

2005/0192495 A1* 9/2005 Makram-Ebeid ........ A61B 6/08
                                                          600/407
2009/0316967 A1   12/2009  Dardenne et al.

FOREIGN PATENT DOCUMENTS

WO     2006129087 A1   12/2006
WO     2012100825 A1    8/2012

OTHER PUBLICATIONS

PCT, Declaration of Non-Establishment of International Search Report, A61B19/00, dated Oct. 27, 2014, 3 pages.
Dastane et al., Hip Offset in Total Hip Arthroplasty: Quantitative Measurement with Navigation, Article,Clin Orthop Relat Res. Feb. 2011; 469(2): 429-436. Published online Sep. 16, 2010 doi: 10.1007/s11999-010-1554-7, pp. 1-9, PMCID: PMC3018189.
Renkawitz et al., In-Vitro Investigation of a Noninvasive Referencing Technology for Computer-assisted Total Hip Arthroplasty, Orthopedics, Apr. 2010, vol. 33 Issue 4., Posted Apr. 1, 2010; DOI: 10.3928/01477447-20100225-10, pp. 1-22.
Renkawitz et al., Leg Length and Offset Measures with a Pinless Femoral Reference Array during THA, Clin Orthop Relat REs. Jul. 2010; 468(7): 1862-1868. Published online Sep. 19, 2009 doi: 10 1007/s11999-009-1086-1, PMCID: PMC2882021.
Renkawitz et al., Experimental Validation of a Pinless Femoral Reference Array for Computer-Assisted Hip Arthroplasty, Published online Nov. 30, 2009 in Wiley InterScience (www.interscience.wiley.com) DOI 10.1002/jor.20139 Published by Wiley Periodicals, Inc. J Orthop Res 28:583-588, 2010.
Murphy et al., Evaluation of a new leg length measurement algorithm in hip arthroplasty, Clin Orthop Relat Res. Oct. 2007; 463:85-9. PMID: 17572632 DOI: 10.1097/BLO.0b013e318126c08f [PubMed—indexed for MEDLINE] (abstract) 1 page.

\* cited by examiner

METHOD FOR ASSISTING THE POSITIONING OF A MEDICAL STRUCTURE ON THE BASIS OF TWO-DIMENSIONAL IMAGE DATA

RELATED APPLICATION DATA

This application is a national phase application of International Application No. PCT/EP2014/052829 filed Feb. 13, 2014, and published in the English language.

The present invention relates to a computer-implemented method for positioning a first medical structure relative to a second medical structure. In particular, the present invention relates to a computer-implemented method for assisting the positioning of an implant relative to a bony structure of a patient.

Methods for establishing the correct position of an implant in joint arthroplasty are usually based on measuring the change in specific points/landmarks between a pre-operative and post-operative situation (for example, leg length and/or offset measurements) or directly comparing measurements in the object space (for example, the distance/depth between the native and post-operative centre of rotation of a hip joint). Examples of leg length and offset measurements for total hip arthroplasty using a comparison between two reference positions of the leg are disclosed in U.S. Pat. No. 7,594,933, U.S. Pat. No. 7,885,705, EP 1 911 421 and WO 2005/000140. These approaches consider overall changes in the leg length and offset (including the femoral and acetabular implant). Documents WO 2006/129087 and US 2009/0316967 disclose methods for aligning joint components relative to each other. Current solutions for determining the leg length and offset on the basis of an analysis of the overall leg situation work well in standard approaches using a pin-based pelvic reference array and a pinless or pin-based femoral reference array. However, such solutions cannot be used in completely pinless approaches, for example when reference arrays are mounted to the cup inserter to be introduced or to a trial stem implant.

Information about the leg length and offset is however very important during surgery in order to avoid patient discomfort, damage to soft-tissue structures and nerves and/or loosening of implants because of significant leg length differences and inadequate offset. In addition, measurements of leg length and offset essentially relate to the overall leg situation, while measurements regarding individual implant components can only be taken by measuring the differences between pre-operatively and post-operatively acquired three-dimensional reference points. In particular, the pre-operative and post-operative centre of rotation (relative to the femoral and/or acetabular side) has to be used. The pre-operative centre of rotation can only be determined to a low level of accuracy, particularly if the acetabular and/or femoral heads are deformed, as is common in total hip arthroplasty patients.

It is the object of the present invention to provide an approach for determining the leg length and offset for individual implant parts without requiring the use of a reference array which has to be rigidly fixed to a patient's bone.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The medical data processing method of the invention comprises the following steps:

acquiring two-dimensional projection image data comprising two-dimensional projection image information describing a two-dimensional projection image of at least the first medical structure (1);

acquiring registration data comprising registration information describing the registration of the two-dimensional projection image with respect to the first medical structure (1);

acquiring, on the basis of said two-dimensional projection image data, two-dimensional position data comprising position information describing the position of at least one base point (3) and at least one reference point (4) in the two-dimensional projection image;

acquiring, on the basis of the two-dimensional position data, positional relationship data comprising positional relationship information describing the positional relationship between the at least one base point (3) and the at least one reference point (4) in the two-dimensional projection image;

acquiring three-dimensional position data comprising position information describing the position of the at least one base point (3) and the at least one reference point (4) in three-dimensional anatomical space, in particular relative to the first medical structure (1);

determining, on the basis of the positional relationship data, the registration data and the three-dimensional position data, three-dimensional reference point correspondence data comprising correspondence information describing whether or not the position of the at least one reference point (4) corresponds to the position of the at least one reference point (4) in the two-dimensional projection image.

For the purposes of this application, leg length and offset are used synonymously for cranial-caudal shifts and medial-lateral shifts, respectively, since the present invention is not limited to hip-joint arthroplasty. Although images taken in an anterior-posterior direction are preferred, the present invention can also be implemented on the basis of two-dimensional images taken from directions other than the anterior-posterior direction, such as a lateral direction (allowing anterior-posterior shifts to be determined) or any oblique directions (allowing any oblique shifts to be determined) such as the direction of the opening plane of the cup implant or the neck of the femoral implant. The determined shifts are then always considered to be one-dimensional differences within the two-dimensional image plane. Cranial-caudal distances (leg length) or medial-lateral distances (offset) are for example differences between the cranial-caudal and medial-lateral positions/co-ordinates.

In other words, landmarks/measurements acquired in projection images, for example pre-operative x-ray images, are compared with landmarks/measurements acquired directly on the patient's anatomy.

The first medical structure can specifically be an anatomical structure of a patient, in particular a bony structure, specifically a patient's pelvis or femur. The second medical structure can either also be an anatomical structure of a patient, in particular a bony structure, specifically a patient's pelvis or femur, or a medical device, in particular an implant or surgical instrument, specifically an artificial hip joint implant or a cutting instrument.

In accordance with a preferred embodiment of the present invention, the two-dimensional projection image is an x-ray image, in particular one taken in an anterior-posterior direction. Such a projection image can however also be taken from any other expedient direction, such as for example a medial-lateral or a cranial-caudal direction.

In order to compare the positional relationship between a base point and a reference point within the projection image with the positional relationship in three-dimensional space, landmarks can be identified for which the cranial-caudal, anterior-posterior and/or medial-lateral position is consistent between the two-dimensional image and three-dimensional space.

In accordance with a preferred embodiment of the present invention, at least one base point is assigned to the first medical structure (for example, the pelvis or the femur) in an invariant positional relationship, wherein the expression "invariant positional relationship" means that the base point and the reference point do not change their position relative to the respective medical structure as long as the projection direction of the projection image has only slightly changed. In addition, at least one reference point is assigned to the second medical structure (for example, another bony structure such as the femur or an artificial hip joint implant) in an invariant positional relationship. Such base points or reference points can for example be any of the prominent landmarks which can be easily palpated by means of a pointer instrument tracked by a medical tracking system. As long as the base points or reference points are assigned to an anatomical structure of a patient, it is beneficial to also be able to identify these points in the two-dimensional projection image, for registration purposes. However, the base points or reference points can also be calculated on the basis of any identifiable structure, as is for example the case with the centre of rotation of the hip joint.

In accordance with a preferred embodiment of the present invention, and in particular for implementing an anterior-posterior projection image, the two-dimensional position data and the positional relationship data can exclusively comprise position information concerning the position of at least one base point and at least one reference point in a cranial-caudal direction and/or in a medial-lateral direction, since measurements of the positional relationship in these directions may be sufficient in order to perform the method of the invention.

In addition, the two-dimensional projection image is registered with respect to the three-dimensional first medical structure, for example on the basis of identifying at least one landmark in both the two-dimensional projection image and the first medical structure. Any prominent feature which can be identified in both the two-dimensional projection image and the three-dimensional anatomical structure can serve as a landmark. It is even possible for a base point or a reference point to serve as a registration landmark. Alternatively or additionally, the registration may be based on any other suitable information. In cases for which the spacial direction in which the two-dimensional image has been taken is known, the registration may be based on the information about the spacial direction of the two-dimensional image. For example, the medial-lateral direction and/or the cranial-caudal direction may be derived from the known spacial direction of a two-dimensional (X-ray) image.

Within the context of the present invention, it is conceivable to "directly" register the two-dimensional projection image with respect to the actual three-dimensional medical structures. On the other hand, "indirect" registration would also be possible, in which the two-dimensional projection image is registered with respect to a three-dimensional model of the medical structure which has in turn been registered with respect to the three-dimensional medical structure itself. Prominent landmarks can help with such a registration.

As already described for the two-dimensional image, a three-dimensional model of the medical structure can also be registered "directly" with respect to the medical structure or "indirectly" with the aid of a registered two-dimensional patient image.

As already explained above, the base points can be palpated on the first medical structure and/or the second medical structure by means of a tracked pointer instrument. However, it is also possible to palpate at least one landmark which has an invariant position relative to the base point or the reference point, whereupon the base point or the reference point can be calculated on the basis of the position of the at least one palpated landmark.

After the position of the at least one reference point corresponding to the position in the two-dimensional projection image has been determined, it is also possible to determine whether the position of the second medical structure (which, for example, comprises at least one reference point) relative to the first medical structure (which, for example, comprises at least one base point) fulfils the condition that the three-dimensional position of the reference point corresponds to the position in the two-dimensional projection image. Any or all of this information can also be indicated to a surgeon so as to assist the latter in positioning the first medical structure relative to the second medical structure.

Both a plurality of base points and a plurality of reference points can also define a geometric structure which can be identified within the two-dimensional projection image and in three-dimensional anatomical space (i.e. with respect to the actual medical structures).

In the following, a more specific explanation of the present invention is provided with respect to hip arthroplasty, without limiting the invention to the specific features explained.

In order to determine the positional relationship in both the two-dimensional projection image and the three-dimensional anatomical space, it is necessary to identify landmarks, hence in a first step, basic anatomical orientations are determined for the two-dimensional projection and the three-dimensional anatomical space. The anterior pelvic plane can for example be determined for measurements on the pelvis in three-dimensional anatomical space, the medial-lateral orientation of the pelvis can for example be determined as the connecting line between the teardrop figures visible in the two-dimensional x-ray projection images, or the mechanical axis (the connecting line between the centre of the femoral head and the centre of the condyles on the femur) can for example be determined for measurements on the femur. The measured positional relationship has to be consistent in both the two-dimensional projection image and the three-dimensional anatomical space.

An implant position, such as for a cup or a femoral implant, can then be determined in the two-dimensional projection image. Specific reference information/landmarks on the implants, for example the centre of rotation of the acetabular and/or femoral implant can be determined. However, this step can be omitted if other identifiable landmarks within the two-dimensional projection image and the three-dimensional anatomical space can be identified. In addition, landmarks on a clearly identifiable horizontal or vertical structure (suitable for a projection image taken in a posterior-anterior direction) can then be determined as a base point, for example a point superior to the top of the acetabular rim which has a clearly identifiable position in a medial/lateral direction, or a point on the upper tip of the greater trochanter which has a clearly identifiable position in a cranial-caudal direction. The cranial-caudal or medial-lateral distance between the reference points on the implant or the anatomy and the base point then have to be determined in the two-dimensional projection image.

As already explained further above, the base points and the reference points can be landmarks on a bony structure or virtual points which have to be calculated (such as the centre of rotation of the implant).

The information obtained from this planning procedure can then be used to verify the proper placement of the implant in the three-dimensional anatomical space. A trackable marker array can be attached to an instrument which is linked to the implant or can be attached directly to the implant, which can be a trial implant. The implant is then moved into place and its positional information relative to the marker array is acquired.

The positional relationship between the base point and the reference point which has been initially determined within the two-dimensional projection image then needs to be determined in the three-dimensional anatomical space. This could be achieved by registering the entire three-dimensional anatomy or by a procedure which detects only the directions which are actually relevant, but to a sufficient level of accuracy. Depending on the definition of the distances, a rough registration could (at least in some directions) be sufficient to accurately measure the distances, even if the registration is not very accurate. This could in particular be the case if the base point and reference point are close to each other, such that if the overall distance for calculating the distances for each anatomical direction is quite short. A rough registration can also be performed by holding the instrument with the marker array in an appropriate direction (for example, holding the cup inserter or reamer in a medial-lateral direction). The base point then has to be palpated/acquired in the three-dimensional anatomical space. The reference point in the three-dimensional anatomical space can either be palpated or determined by pre-calibrating an instrument/marker array for which the relationship between the marker array and the reference point is known, for example from an implant/instrument database.

Lastly, the positional relationship—specifically, the directional distance—between the reference point and the base point is calculated and compared with the corresponding positional relationship/distance measured in the two-dimensional projection image.

This procedure can be performed intra-operatively. Positional data acquired within the three-dimensional anatomical space can for example be transformed back into two-dimensional positional data within the projection image, and vice versa. In so doing, it is possible to verify the correct position of the second medical structure with respect to the first medical structure. It is also conceivable for this to be performed iteratively until a correct position of the medical structures relative to each other has been found.

Specific examples of ways in which the implant position can be optimised are presented in the following.

The correct depth of the cup implant could be detected by using a point on the flat surface directly superior to the top (twelve o'clock position) of the acetabular rim or a point directly inferior to the bottom (six o'clock position) of the acetabular rim on the ischium as the base point, and the centre of rotation of the cup implant as the reference point. The directional distance (depth) could then be measured in a medial-lateral direction. On the basis of the planning in the two-dimensional x-ray image, a proper depth position can be found which prevents the implant from penetrating the medial wall of the acetabulum. The cranial-caudal shift in the cup implant can be determined by comparing its centre of rotation as a reference point with a point at the bottom or top lateral edge of the acetabular rim, the cranial-caudal position of which is clearly identifiable in both the two-dimensional projection image and the three-dimensional anatomical space. The basic set-up for these measurements could be established either after the cup implant has been moved into place with a navigated inserter still fixedly attached to the implant or by using another tool such as a cup reamer, a cup inserter with a trial implant which is not yet fixed, or any other specifically designed tool which is held approximately in a defined direction such as the medial-lateral direction. Alternatively, a reference array which is rigidly fixed to the pelvic bone, as is the case in established navigation systems, can also be used.

Similar measurements could be obtained on the femoral side, for example by using the uppermost tip of the femoral head and/or the furthest lateral/medial extent of the greater trochanter as base points for the cranial-caudal (leg length) and medial-lateral (offset) measurements, respectively. The height and medial-lateral position of the implant should again be adequately planned in the two-dimensional x-ray images. A trial implant or any other appropriate tool can be inserted into the femur after the femoral canal has been opened. A marker array can be attached to the trial implant/tool in a fixed relationship, thus allowing the virtual position of the centre of rotation to be determined. The base points can be acquired in relation to this marker array, and the directional distances (for example, the cranial-caudal and/or medial-lateral distances) from the reference points can be calculated. A comparison with the planned distances can then for example be used to determine whether an additional resection of the femoral head, more extensive reaming of the femoral canal, or simply a change in the implant design is necessary.

This approach can also be used to establish a planned position for the neck cut in total hip arthroplasty without having to have a (trial) stem already in place. A temporary reference (for example, a marker array mounted on a clamp which is to be fixed around the femoral neck) can then be used to obtain landmark data in the three-dimensional anatomical space. The reference point could then for example be a point defining the upper or lower edge of the intended neck cut. The base point could for example be a point on the top of the femoral head or the greater trochanter, when measuring the height (cranial-caudal position) of the neck cut, or for example a point at the lateral edge of the greater trochanter when defining the medial-lateral position of the neck cut. FIG. 1 shows a sketch of this particular realisation. Alternatively, oblique orientations (for example, orthogonal to the planned neck axis or in a 135° direction in relation to the mechanical/cranial-caudal axis) could also be used. The implant position, and subsequently also the position of the neck cut, could be initially planned in the x-rays. In the three-dimensional anatomical space, the base point could be defined in a first step. The position of the reference points (neck cut position) could then be marked using a navigated tool and some kind of pen or directly using a navigated saw. This process could also be used to verify and where applicable refine the neck cut.

The approach described can also be adapted for measuring the overall leg length and offset changes. A measurement between a (directionally) identifiable point (in the two-dimensional projection and three-dimensional anatomical space) on the pelvis and the femur (one being used as the base point, the other as the reference point) then has to be performed and the distance between these points calculated. In the anatomical space, the relative orientation between the femur and the pelvis has to be identified, and a relative orientation equivalent to the two-dimensional image has to be achieved. This could be achieved either by measuring the relative alignment of the leg between the two-dimensional projection and the three-dimensional anatomical space and/or aiding the surgeon in finding the proper alignment, or by correcting the alignment virtually, which is for example possible if the centre of rotation of the implant can be detected appropriately and a rotation around the centre of rotation can be performed until the anatomical alignment matches the alignment given in the two-dimensional projection image.

It is of course also possible to combine different directional measurements and different base points and reference points in order to position the implants in more detail or to make the approach more robust/accurate, for example by averaging between different aspects of this information or by performing consistency checks.

This technique can be used to directly optimise implant positions and orientations as well as implant parameters (for example, liner types or neck designs). It can also be combined with other techniques, to optimise implant positioning and design, for example when optimising functional and/or biomechanical parameters such as range of motion, cup coverage, anatomical alignment, cup orientation and biomechanical stability. For this purpose, the desired/planned leg length and offset information can be used as additional parameters or constraints, to optimise the functional and/or biomechanical parameters. This can also be performed in an iterative process. For this purpose, the currently determined information in the three-dimensional anatomical space can be transferred into the two-dimensional projection image. This can include the measured distance information, but also other parameters measured in the three-dimensional anatomical space such as implant orientation, etc. Planning can then be adjusted in view of the current situation in the two-dimensional projection image. The intra-operative situation can in turn be adapted in accordance with the adjusted planning. These steps can then be iterated in order to further refine the planning/insertion of the implants.

In general, this particular technique can be used to transfer information measured in the three-dimensional anatomical space into a two-dimensional projection image and to refine planning for implants on the basis of this information, i.e. the current leg length and offset information and/or simply standard navigation information (such as for example cup orientation) can be transferred from the anatomical space into the planned surgery being developed on the basis of the x-ray image, wherein the surgeon can then directly check whether the current position is appropriate for the individual patient; this has the advantage that the surgeon can better judge the individual anatomy on the basis of the x-ray images than on the basis of image-free navigation techniques alone.

The technique can essentially be combined with any suitable form of tracking/point acquisition (such as for example optical tracking, electromagnetic tracking or gyro/inertial sensing) and imaging (such as for example pre-operative x-rays, intra-operative x-rays using mobile C-arms, scout views or digitally reconstructed radiographs from CT images). Three-dimensional anatomical space can directly refer to landmark information at the actual physical anatomical structure such as the pelvis, as well as to an acquired three-dimensional image of the anatomical structure, or landmark or general coordinate information in three-dimensional imaging data like CT or MRI images. It can also be applied to any type of joint surgery, including for example total joint arthroplasty, resurfacing techniques and osteotomy, and to any anatomical joints (such as for example the hip, knee, shoulder, elbow, ankle and vertebral facet joints) and regions (such as for example the pelvis, femur, tibia and vertebrae).

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purposes of this document, a computer is a technical computer which in particular comprises technical, in particular tangible components, in particular mechanical and/or electronic components. Any device mentioned as such in this document is a technical and in particular tangible device.

The present invention is also directed to a navigation system for computer-assisted surgery. This navigation system preferably comprises the aforementioned computer for processing the data provided in accordance with the data processing method as described in any one of the preceding embodiments. The navigation system preferably comprises a detection device for detecting the position of the detection points which represent the base points and reference points, in order to generate detection signals and to supply the generated detection signals to the computer, such that the computer can determine the absolute base point data and absolute reference point data on the basis of the detection signals received. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (such as for example a visual signal, an audio signal and/or a vibration signal). One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the centre of rotation of the femur when moved relative to the acetabulum.

A detection point is in particular a point on the surface of the anatomical structure which is detected, for example by a pointer.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. The invention is instead directed in particular to positioning the tool relative to the medical implant, which may be outside the patient's body. For this reason alone, no surgical or therapeutic activity and in particular no surgical or therapeutic step is necessitated or implied by carrying out the invention.

In the following, the invention is described with reference to the figures which represent preferred embodiments of the invention, without limiting the invention to the specific features shown in the figures.

Figure 1:
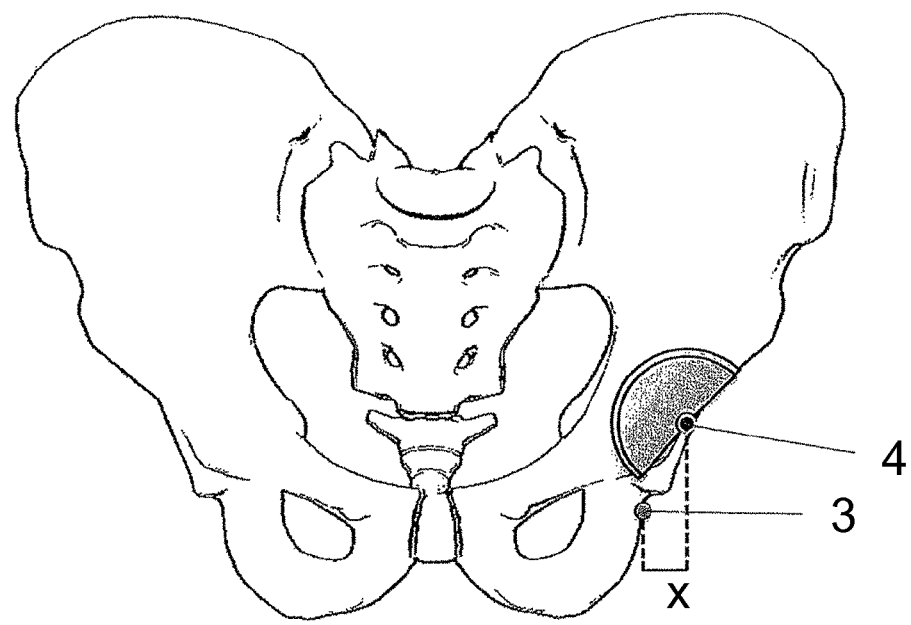
FIG. 1 shows the cup of an artificial hip joint implant, including its centre of rotation as a reference point, in relation to a pelvis comprising a base point.

FIG. 1 shows a patient's pelvis together with the cup of an artificial hip joint implant. The centre of rotation of the cup constitutes a reference point 4. A point directly inferior to the bottom of the acetabular rim constitutes a base point 3. The distance x between the base point 3 and the reference point 4 in a medial-lateral direction can be easily determined from an anterior-posterior x-ray image (incorporating the centre of rotation of the native hip joint) as well as in a three-dimensional anatomical space, for example by palpating the point 3 and calculating the point 4 on the basis of the position of other points or landmarks palpated by means of a tracked pointer instrument. The medial-lateral distance x can therefore be measured in the two-dimensional projection image and in the three-dimensional anatomical space. The measurement in the two-dimensional projection image can however also be performed as a first step, once planning has been finalised, and then used to track the position in the anatomical space. Conversely, the medial-lateral distance in the anatomical space could also be transferred back into the two-dimensional projection image and used to check whether the implant would penetrate the medial wall of the acetabulum, since the distance in a medial-lateral direction between the cup and critical structures of the medial wall of the acetabulum can be better identified in the two-dimensional projection image.

Figure 2:
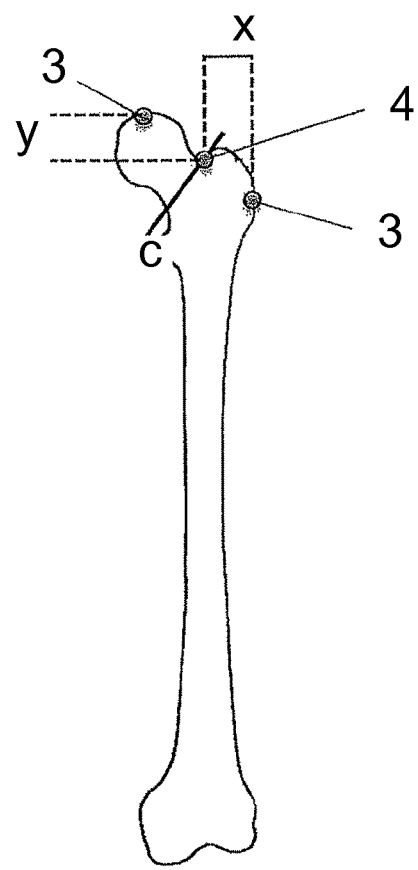
FIG. 2 shows a femur comprising two base points and a reference point which define a cutting plane.

FIG. 2 shows a situation in which the position of a cutting plane comprising a reference point 4 can be determined relative to prominent base points 3 on the femur, wherein the positional relationship between the reference point 4 and a base point 3 in a medial-lateral direction is indicated as x, and the positional relationship between the reference point 4 and a base point 3 in a cranial-caudal direction is indicated as y. The correct position (i.e. the correct spatial location and/or orientation) of the plane with respect to the base points 3 can be determined with the aid of the steps described further above.

The invention claimed is:

1. A medical data-processing system for assisting a positioning of a first medical structure relative to a second medical structure, the system comprising a navigation system, a display, and a computer having a processor, the processor being configured to:
   acquire, at the processor, two-dimensional projection image data comprising two-dimensional projection image information describing a two-dimensional projection image of at least the first medical structure;
   acquire, at the processor, registration data comprising registration information describing a registration of the two-dimensional projection image with respect to the first medical structure;
   acquire, at the processor and on the basis of said two-dimensional projection image data, two-dimensional position data comprising position information describing a position of at least one base point and at least one reference point in the two-dimensional projection image;
   acquire, at the processor and on the basis of the two-dimensional position data, positional relationship data comprising positional relationship information describing a directional distance between the at least one base point and the at least one reference point in the two-dimensional projection image;
   acquire, at the processor from the navigation system, three-dimensional position data comprising position information describing a position of the at least one base point and the at least one reference point in a three-dimensional anatomical space;
   determine, by the processor and on the basis of the positional relationship data, the registration data and the three-dimensional position data, three-dimensional reference point correspondence data comprising correspondence information describing a directional distance between the at least one base point and the at least one reference point in the three-dimensional anatomical space that is consistent with the directional distance in the two-dimensional projection image; and
   output the three-dimensional reference point correspondence data to the display thereby assisting a surgeon in positioning the first medical structure relative to the second medical structure.

2. A computer-implemented medical method, using a medical system comprising a navigation system, a display, and a computer having a processor, for assisting a positioning of a first medical structure relative to a second medical structure, the method comprising executing, on the processor, the steps of:
   acquiring, at the processor, two-dimensional projection image data comprising two-dimensional projection image information describing a two-dimensional projection image of at least the first medical structure;
   acquiring, at the processor, registration data comprising registration information describing a registration of the two-dimensional projection image with respect to the first medical structure;
   acquiring, at the processor and on the basis of said two-dimensional projection image data, two-dimensional position data comprising position information describing a position of at least one base point and at least one reference point in the two-dimensional projection image;
   acquiring, at the processor and on the basis of the two-dimensional position data, positional relationship data comprising positional relationship information describing a directional distance between the at least one base point and the at least one reference point in the two-dimensional projection image;
   acquiring, at the processor from the navigation system, three-dimensional position data comprising position information describing a position of the at least one base point and the at least one reference point in a three-dimensional anatomical space;
   determining, by the processor and on the basis of the positional relationship data, the registration data and the three-dimensional position data, three-dimensional reference point correspondence data comprising correspondence information describing a directional distance between the at least one base point and the at least one reference point in the three-dimensional anatomical space that is consistent with the directional distance in the two-dimensional projection image;
   outputting the three-dimensional reference point correspondence data to the display thereby assisting a surgeon in positioning the first medical structure relative to the second medical structure.

3. The method according to claim 2, wherein the first medical structure is an anatomical structure of an associated patient.

4. The method according to claim 2, wherein the second medical structure is selected from a group consisting of:
   an anatomical structure of an associated patient;
   an implant or a surgical instrument.

5. The method according to claim 2, wherein the two-dimensional projection image is an x-ray image made in an anterior-posterior direction.

6. The method according to claim 2, wherein the at least one base point is assigned to the first medical structure in an invariant positional relationship and/or the at least one reference point is assigned to the second medical structure in an invariant positional relationship.

7. The method according to claim 2, wherein the two-dimensional position data and the positional relationship data comprise position information concerning the position of the at least one base point and the at least one reference point in a cranial-caudal direction and/or in a medial-lateral direction and/or in an anterior-posterior direction.

8. The method according to claim 2, wherein the two-dimensional projection image is registered with respect to the first medical structure on the basis of identifying at least one landmark in both the two-dimensional projection image and the first medical structure.

9. The method according to claim 2, wherein the acquiring the three-dimensional position data is based on palpating the at least one base point and/or the at least one reference point.

10. The method according to claim 2, wherein the acquiring the three-dimensional position data is based on palpating at least one landmark that has an invariant position relative to the at least one base point or the at least one reference point.

11. The method according to claim 2, wherein the determining the three-dimensional reference point position data of the at least one reference point comprises determining whether or not a correspondence between the second medical structure and the first medical structure fulfils a condition that the three-dimensional position of the at least one reference point approximately corresponds to the position of the at least one reference point in the two-dimensional projection image.

12. The method according to claim 2, wherein a plurality of base points and/or a plurality of reference points define at least one geometric structure that can be identified within the two-dimensional projection image, the at least one geometric structure comprising one or more lines, curves, planes or curved surfaces.

13. The method according to claim 2, wherein the acquiring the three-dimensional position data comprises defining a three-dimensional space, and wherein a spatial position of the first and the second medical structure is determined relative to said three-dimensional space.

14. The method according to claim 13, wherein a plurality of base points and/or a plurality of reference points define at least one geometric structure that can be identified within said three-dimensional space, the at least one geometric structure comprising one or more lines, curves, planes or curved surfaces.

15. The method according to claim 2, wherein the determining the three-dimensional reference point correspondence data comprises transforming the three-dimensional position data into the two-dimensional position data and/or transforming the two-dimensional position data into the three-dimensional position data.

16. A non-transitory computer-readable program storage medium storing a computer program for assisting a positioning of a first medical structure relative to a second medical structure, using a medical system comprising a navigation system, a display, and a computer having a processor, which, when executed on the processor or loaded into the memory of the computer, causes the computer to:

acquire, at the processor, two-dimensional projection image data comprising two-dimensional projection image information describing a two-dimensional projection image of at least the first medical structure;

acquire, at the processor, registration data comprising registration information describing a registration of the two-dimensional projection image with respect to the first medical structure;

acquire, at the processor and on the basis of said two-dimensional projection image data, two-dimensional position data comprising position information describing a position of at least one base point and at least one reference point in the two-dimensional projection image;

acquire, at the processor and on the basis of the two-dimensional position data, positional relationship data comprising positional relationship information describing a directional distance between the at least one base point and the at least one reference point in the two-dimensional projection image;

acquire, at the processor from the navigation system, three-dimensional position data comprising position information describing a position of the at least one base point and the at least one reference point in a three-dimensional anatomical space;

determine, by the processor and on the basis of the positional relationship data, the registration data and the three-dimensional position data, three-dimensional reference point correspondence data comprising correspondence information describing a directional distance between the at least one base point and the at least one reference point in the three-dimensional anatomical space that is consistent with the directional distance in the two-dimensional projection image; and output the three-dimensional reference point correspondence data to the display thereby assisting a surgeon in positioning the first medical structure relative to the second medical structure.

17. A computer comprising the non-transitory computer-readable program storage medium according to claim 16.

* * * * *